United States Patent [19]
Griffith et al.

[11] Patent Number: 5,134,367
[45] Date of Patent: Jul. 28, 1992

[54] ROTATING EDDY CURRENT ROLLER HEAD FOR INSPECTING AND PROFILING TUBING HAVING TWO SEPARATE CROSS WOUND COILS

[75] Inventors: John C. Griffith, Lynchburg; Ivan G. Masters, Forest, both of Va.

[73] Assignee: The Babcock & Wilcox Company, New Orleans, La.

[21] Appl. No.: 671,321

[22] Filed: Mar. 19, 1991

[51] Int. Cl.⁵ .............................................. G01N 27/90
[52] U.S. Cl. ..................................... 324/220; 324/262
[58] Field of Search ................................. 324/219–221, 324/225, 226, 262, 243, 242, 236, 237, 238

[56] References Cited

U.S. PATENT DOCUMENTS 3,611,120 10/1971 Forster ................................. 324/225
4,625,165 11/1986 Rothstein ............................. 324/220
4,937,524 6/1990 Fasnacht .............................. 324/220

Primary Examiner—Walter E. Snow
Attorney, Agent, or Firm—R. J. Edwards; D. Neil LaHaye

[57] ABSTRACT

A rotating cross wound eddy current head for inspecting tubing. A main body portion has a coil mounting arm pivotally mounted in a bore on the main body portion that allows for radial movement of the arm. A cross wound eddy current coil is mounted adjacent the opposite end of the arm from the pivotal mounting point. Opposing magnets mounted in the main body portion and coil mounting arm bias the arm and coil radially outward so that the coil tracks the surface of the tube being inspected and only reads one point on the tube. A helical inspection path is provided by moving the head axially through the tube while simultaneously rotating the head.

7 Claims, 1 Drawing Sheet

ROTATING EDDY CURRENT ROLLER HEAD FOR INSPECTING AND PROFILING TUBING HAVING TWO SEPARATE CROSS WOUND COILS

BACKGROUND OF THE INVENTION

1. Field of the Invention

The present invention is generally related to nondestructive examination of heat exchanger tubing and more particularly to eddy current testing of such tubing.

2. General Background

In steam generators used for energy production, coolant from the nuclear reactor travels through the tubes and transfers heat through the tubes to the secondary coolant in the steam generator. Due to the harsh operating environment, it is not uncommon for tubes to develop cracking, pitting or corrosion on the inner or outer diameter of the tube that could lead to a leaking tube and mixing of primary and secondary coolant. Damage to tubes can also result from loose parts in the system. In plants that operate close to their design capacity, repair of damaged tubes to keep them in service is preferred to plugging these tubes. Installation of a sleeve that bridges the damaged area inside the original tube is a commonly used repair since it essentially maintains the heat exchange surface area. Sleeve installation for one type of sleeve is accomplished by positioning the sleeve, with a charge loaded in the sleeve, inside the tube to bridge the damaged area and firing the charge. When the charge is fired, part of the sleeve outer diameter impacts the original tube inner diameter with a force that causes a band of metallurgical bonding. This band forms a fluid seal. The expanded area of the sleeve and tube is then heat treated to relieve any stresses that could lead to stress corrosion cracking in the tube. Other sleeve installations use a roll expanded joint or a TIG or laser welded joint.

Eddy Current testing has become a standard method for nondestructive evaluation (NDE) of heat exchanger tubing. Typically a differential bobbin coil probe with the coil axis coaxial with the tube axis is used for the majority of tubing inspection.

One of the most challenging nondestructive examination (NDE) areas of the steam generator is the original tube wall behind the sleeve ends where the tube still serves as the pressure boundary between the primary and secondary side coolant, and the joint area proper (the point of expansion and metallurgical bonding between the sleeve and original tube). The parent tube area is shielded from the NDE sensor by the sleeve. Inspection in this area is further complicated by geometry signals from the sleeve end and the joint, which are ordinarily many times the amplitude of the target flaws to be detected. This makes the detection of true degradation signals more difficult. The sleeve joint presents a different set of challenges to confirm absence of flaws in the parent tube or sleeve within the weld area. This is due to the thickness of the wall created by the joint. It is also necessary to measure the diametrical profile of the joint as a process verification requirement.

A differential cross wound probe was developed to minimize the residual (unwanted) signal response caused by uniform circumferential surface discontinuities such as those at the sleeve ends or attachment locations. The cross wound probe is similar in design to a differential bobbin coil probe except that each coil consists of two 180 degree segments which are offset vertically. The second coil is a mirror image of the first coil across the center of the probe. When the probe is in a uniform circumferential surface discontinuity, any impedance change reflected into the upper 180 degree segment of the first coil will be partially canceled by a similar impedance change in the second coil segment at the same elevation. However, the differential bobbin cross wound probe still suffers from residual geometry induced noise and loss of sensitivity in areas of increased tube ID since the coil remains radially centered in the tube. This probe integrates the eddy current response for the entire circumference of the tube or sleeve at one elevation. This is due to the fact that the probe is centered as it is pulled through the sleeve and that diametrically opposed poles of each coil are substantially equidistant from the wall of the sleeve or tube being examined. The overall effect is a reduced sensitivity and higher residual noise than the current invention.

Another Eddy Current development driven by the need to improve signal to noise ratio and to provide better defect imaging was the development of a rotating pancake coil (RPC) probe technology. The RPC is ordinarily mounted on a motorized sheath which allows the coil to be simultaneously rotated and translated through the tube thereby developing a helical scan of the tube surface. The pancake eddy current coil axis is normal to the tube ID surface. The coil is mounted in an articulating mechanism allowing the coil to follow the ID surface contour, and to maintain a relatively constant coil liftoff. This inspection technology provides two dimensional defect imaging, better elimination of geometry induced signals due to the surface following characteristic, and thus better detection sensitivity for certain tube indications. However, its sensitivity to outside diameter initiated degradation in thicker or layered material is very limited.

From the above, it can be seen that a need exists for a nondestructive examination apparatus that is more effective in examining thicker walls such as that created at a sleeve/tube joint and the sleeve and original tube behind the sleeve on either end of the joint or in any other thicker or multiple wall tubing, particularly in the presence of ID geometry changes. There is also the need to measure the ID profile in sleeve attachment areas to verify proper installation.

SUMMARY OF THE INVENTION

The present invention addresses the aforementioned problem in a straightforward manner. What is provided is a rotating cross wound eddy current head. A body riding between two wheels is attached to a sheath that provides body rotation and is pushed or pulled through the tube by an external positioning system driver. A lever arm pivotally mounted in the head has two cross wound coils mounted thereon. Opposing magnets mounted in the body and lever arm keep the coils forced outward and in close proximity to the surface being inspected. A cover over the coils prevents direct contact of the coils with the inspection surface to prevent unnecessary coil wear. An end cap mounted on the lever arm adjacent to each side of the coils provides for a smooth transition over obstacles such as sleeve ends.

BRIEF DESCRIPTION OF THE DRAWINGS

For a further understanding of the nature and objects of the present invention, reference should be had to the following description taken in conjunction with the accompanying drawings in which like parts are given like reference numerals, and wherein.

DETAILED DESCRIPTION OF THE PREFERRED EMBODIMENT

Figure 1:
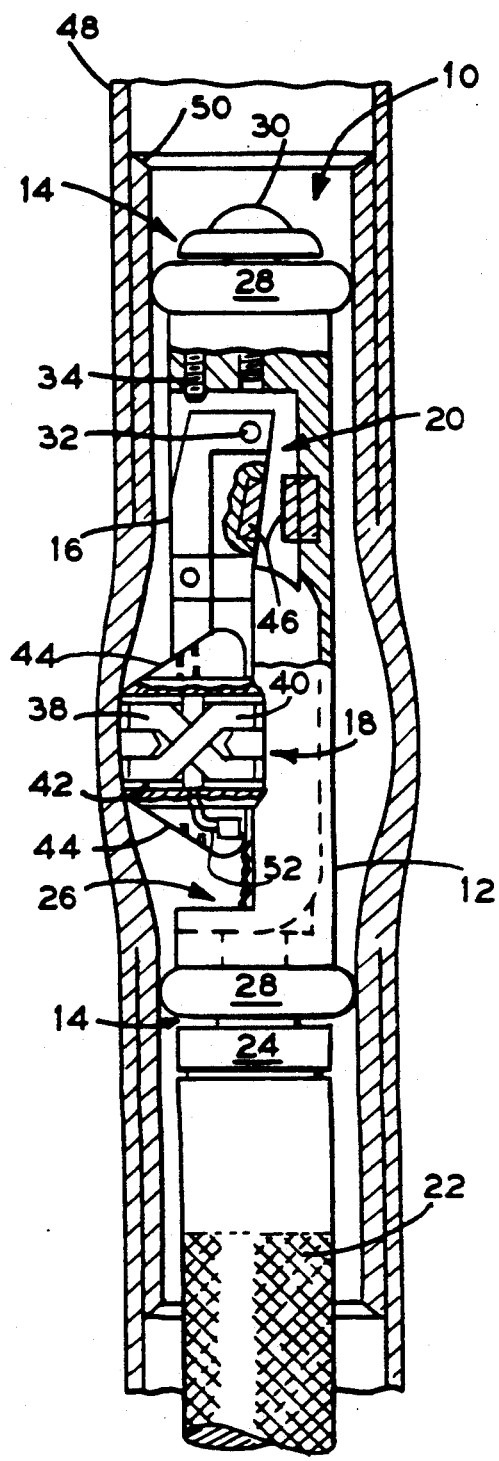
FIG. 1 is a side sectional view illustrating the invention positioned in a tube where a sleeve repair has been performed.

Referring to the drawings, it can be seen in FIG. 1 that the invention is generally referred to by the numeral 10. Rotating cross wound eddy current head 10 is generally comprised of main body portion 12, means 14 for centering main body portion 12 in the tube/sleeve being inspected, coil mounting arm 16, eddy current coil set 18, and means 20 for biasing eddy current coil set 18 radially outward to track the inner surface of the tube/sleeve being inspected.

Main body portion 12 is attached to drive mechanism 22 at connector 24. Drive mechanism 22 may be formed from any of several suitable mechanisms well known in the art for pushing and pulling an inspection apparatus through a tube while the drive mechanism is simultaneously being rotated to cause rotation of the inspection apparatus. Drive mechanism 22 is generally represented in FIG. 1 as a semi-rigid sheath. Equipment external of the tube and heat exchanger known in the art is used to drive the sheath and rotate the inspection apparatus attached thereto as well as to determine the position of the inspection apparatus in the tube being inspected. Main body portion 12 is provided with a cutout or bore 26 sized to receive coil mounting arm 16. Bore 26 extends substantially along the central section of main body portion 12. Main body portion 12 is provided with a narrow radius adjacent connector 24 and at the opposite end for receiving centering means 14.

Means 14 for centering main body portion 12 is comprised of wheels 28 rotatably mounted on the narrow radius mentioned above. Wheels 28 have their axis of rotation coaxial with the longitudinal axis of main body portion 12 and are sized in accordance with the interior diameter of the tube to be inspected. End cap 30 is attached to the narrow radius at the end of main body portion 12 opposite connector 24 and serves to retain wheel 28 at that end in its installed position.

Coil mounting arm 16 is pivotally mounted at one end to main body portion 12 at one end of bore 26 on pivot pin 32. This allows pivoting of coil mounting arm 16 and eddy current coil set 18 in a radial direction relative to main body portion 12 and the tube being inspected. Limit screw 34 extends axially from main body portion 12 into bore 26 and provides a means of limiting the radial movement of coil mounting arm 16 and eddy current coil 18 outward from main body portion 12 toward the tube being inspected.

Figure 2A:
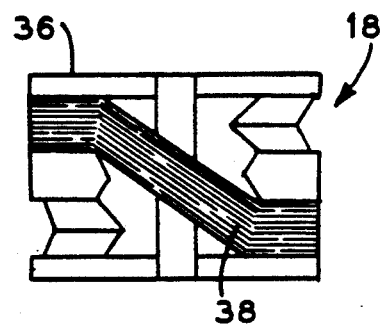
FIGS. 2A and 2B illustrate the winding pattern of the coils on the coil form as used in the present invention.
Figure 2B:
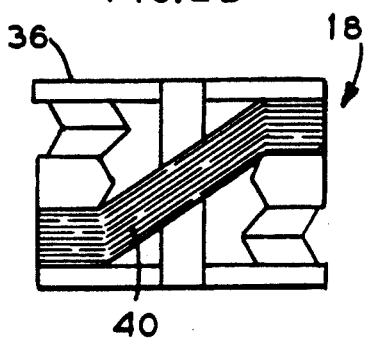

Eddy current coil set 18 is mounted on coil mounting arm 16 adjacent the end opposite that of pivot pin 32. As best seen in FIG. 2A, B, eddy current coil set 18 is comprised of a ferrite core or form 36 such as ferritron having two separate winding patterns 38 and 40 positioned thereon. This produces two coils on form 36 and results in the formation of a cross wound eddy current coil. As seen in FIG. 1, eddy current coil set 18 is mounted so that the ends of windings 38, 40 face radially toward the tube being inspected. To protect coil set 18 from wear it is preferable that cover 42 be provided to prevent direct contact of the coil with the tube being inspected. Cover 42 may be formed from a thin non-metallic material suitable for the intended use of the invention. Coil end caps 44 are fastened on coil mounting arm 16 immediately adjacent opposite sides of eddy current coil set 18. Each coil end cap 44 is substantially triangular in cross section and sized and mounted so that the slope of their sides prevents eddy current coil set 18 from hanging up on any obstacle in the tube being inspected and also provides for a smooth movement and transition over any obstacles that may be encountered. Coil end caps 44 may be formed from any suitable material such as Delrin ® or nylon.

Means 20 for biasing eddy current coil radially outward to track the inner surface of the tube being inspected is comprised of opposing magnets 46. One of magnets 46 is rigidly mounted in main body portion 12 and the other magnet is rigidly mounted in coil mounting arm 16 so as to face the magnet in main body portion 12. The magnets are mounted so that like poles of the magnets face each other. In this manner, the repulsive force generated between the magnets urges coil mounting arm 16 and eddy current coil 18 radially outward for tracking the inner surface of the tube being inspected.

In operation, rotating cross wound eddy current head 10 is attached to drive mechanism 22 by connector 24 and inserted into tube 48 and sleeve 50 to be inspected. Wheels 28 provide for centering action and ease of rotation as head 10 is moved axially through the tube while simultaneously being rotated by driving mechanism 22. This results in a helical inspection path by eddy current coil set 18. Opposing magnets 46 cause one end of coil mounting arm 16 and eddy current coil set 18 to be biased radially outward and track the inner surface of tube 48 and sleeve 50. Coil end caps 44 provide for a smooth transition over each end of sleeve 50 and any other obstacles that may be encountered. Electronic equipment known in the industry is attached to the end of wiring harness 52 that allows eddy current coil set 18 to generate and receive signals which are processed by the equipment as the invention is pulled and rotated through the tube and sleeve. The rotating cross wound coil of eddy current coil set 18 is more effective at generating and receiving signals that allow the operator to distinguish the ends of the sleeve from the tube, determine the presence of defects on the inner or outer diameter of the sleeve or tube at the non-bonded area of the sleeve and tube, and to determine the presence of defects on the inner or outer surface of the thicker, bonded area between the sleeve and tube than the conventional cross wound. This is mainly due to the fact that conventional cross wound heads are not rotated, are not surface following, and read the entire circumference of the tube. In contrast, the present invention rotates and positions the coil adjacent to a unique circumferential location so as to read only a single point on the tube to provide a helical inspection path.

Because many varying and differing embodiments may be made within the scope of the inventive concept herein taught and because many modifications may be made in the embodiment herein detailed in accordance with the descriptive requirement of the law, it is to be understood that the details herein are to be interpreted as illustrative and not in a limiting sense.

What is claimed as invention is:

1. A rotating cross wound eddy current head for inspecting and profiling tubing, comprising:

a. a main body portion having a bore that extends substantially along its central section;
b. means for centering said main body portion in tubing being inspected;
c. a coil mounting arm pivotally mounted at one end of said bore for radial movement of said arm relative to said main body portion;
d. a cross wound eddy current coil mounted adjacent the end of said coil mounting arm, said cross wound eddy current coil being formed from two separate windings positioned such that the ends of the windings face radially toward the tube being inspected and profiled; and
e. means for biasing said coil mounting arm and said eddy current coil radially outward to track the inner surface of the tube being inspected.

2. The rotating cross wound eddy current head of claim 1, wherein said means for centering said main body portion comprises a wheel rotatably mounted adjacent each end of said main body portion.

3. The rotating cross wound eddy current head of claim 1, wherein said means for biasing said coil mounting arm and said eddy current coil radially outward comprises opposing magnets mounted in said main body portion and said coil mounting arm.

4. The rotating cross wound eddy current head of claim 1, further comprising coil end caps mounted on either side of the two windings forming said cross wound eddy current coil.

5. A rotating cross wound eddy current head for inspecting and profiling tubing, comprising:
a. a main body portion having a bore that extends substantially along its central section;
b. means for centering said main body portion in tubing being inspected comprising a wheel rotatably mounted adjacent each end of said main body portion;
c. a coil mounting arm pivotally mounted at one end of said bore for radial movement of said arm relative to said main body portion;
d. a cross wound eddy current coil mounted adjacent the end of said coil mounting arm, said cross wound eddy current coil being formed from two separate windings positioned such that the ends of the windings face radially toward the tube being inspected and profiled; and
e. opposing magnets mounted in said main body portion and said coil mounting arm whereby said arm and coil are biased radially outward to track the inner surface of the tube being inspected.

6. The rotating cross wound eddy current head of claim 5, further comprising coil end caps mounted on either side of the two windings forming said cross wound eddy current coil.

7. A method of inspecting tubing, comprising:
a. inserting into the tubing an inspection head having a cross wound eddy current coil formed from two separate windings positioned such that the ends of the windings face radially toward the tube being inspected that reads a single point of the tubing;
b. moving said inspection head axially through said tubing while simultaneously rotating said inspection head and biasing the coil radially outward to track the tube whereby said cross wound eddy current coil travels through said tubing in a helical inspection path; and
c. generating and receiving signals through said cross wound eddy current coil whereby the material condition and profile of said tubing may be determined.

* * * * *